US012734142B2

(12) United States Patent
Pahan

(10) Patent No.: US 12,734,142 B2
(45) Date of Patent: Sep. 15, 2026

(54) USE OF A CINNAMEIN COMPOSITION FOR THE TREATMENT OF GLYCINE ENCEPHALOPATHY AND UREA CYCLE DISORDERS

(71) Applicant: Rush University Medical Center, Chicago, IL (US)

(72) Inventor: Kalipada Pahan, Skokie, IL (US)

( * ) Notice: Subject to any disclaimer, the term of this patent is extended or adjusted under 35 U.S.C. 154(b) by 572 days.

(21) Appl. No.: 18/306,697

(22) Filed: Apr. 25, 2023

(65) Prior Publication Data

US 2023/0255910 A1 Aug. 17, 2023

Related U.S. Application Data

(63) Continuation-in-part of application No. PCT/US2021/056799, filed on Oct. 27, 2021.

(60) Provisional application No. 63/106,456, filed on Oct. 28, 2020.

(51) Int. Cl.
*A61K 31/192* (2006.01)
*A61K 9/00* (2006.01)
*A61P 3/00* (2006.01)

(52) U.S. Cl.
CPC .......... *A61K 31/192* (2013.01); *A61K 9/0053* (2013.01); *A61P 3/00* (2018.01)

(58) Field of Classification Search
CPC .................................................... A61K 31/192
See application file for complete search history.

(56) References Cited

U.S. PATENT DOCUMENTS

| | | | | |
|---|---|---|---|---|
| 6,011,000 | A * | 1/2000 | Perrine | A61K 31/405 514/513 |
| 6,107,410 | A | 8/2000 | Waki et al. | |
| 2006/0045894 | A1 * | 3/2006 | Brown | A61Q 19/08 424/760 |
| 2016/0331714 | A1 | 11/2016 | Pahan | |

FOREIGN PATENT DOCUMENTS

| | | | |
|---|---|---|---|
| WO | 2015109215 | A1 | 7/2015 |
| WO | 2019070478 | A1 | 4/2019 |
| WO | 2020/176432 | A1 | 9/2020 |
| WO | 2021170982 | A1 | 9/2021 |

OTHER PUBLICATIONS

International Search Report dated Feb. 1, 2022 issued in PCT/US/21/56799 (2 pages).

Husson, et al., Efficacy and safety of i.v sodium benzoate in urea cycle disorders: a multicentre retrospective study, Sep. 2016 [Retrieved Dec. 27, 2021] Retrieved from Internet URLhttps://www.ncbi.ntm,nih.gov/pmc/articles/PMC5034629/pdf/13023_2016_Article_513.pdf )(.

Supplementary Partial European Search Report, European Patent Office, European Patent Application No. 21887415, filed Jul. 18, 2024, 4 pages.

Kalipada Pahan: "Immunomodulation of experimental allergic encephalomyelitis by cinnamon metabolite sodium benzoate," Immunopharmacology and Immunotoxicology, vol. 33, No. 4, Dec. 1, 2011, pp. 586-593.

Leung Kit-yi et al: "hyperglycinemia", Journal of Inherited Metabolic Disease., vol. 43, No. 6, Aug. 11, 2020, pp. 1186-1198.

The RIFM Expert Panel Belsito et al: "A toxicologi dermatologic assessment of related esters and alcohols of and cinnamyl alcohol when used as fragrance ingredients", Food and Chemical Toxicology, Pergamon, GB vol. 45, No. 1, Jan. 1, 2007, pp. S1-S23.

Johannes, H. et al., "Suggested guidelines for the diagnosis and management of urea cycle disorders: First revision," Journal of Inherited Metabolic Disease, 2019, 42(6), pp. 1192-1230.

Husson et al., "Efficacy and safety of i.v. sodium benzoate in urea cycle disorders: a multicentre retrospective study", Orphanet Journal of Rare Diseases, 2016, pp. 1-8.

* cited by examiner

*Primary Examiner* — Rei Tsang Shiao
(74) *Attorney, Agent, or Firm* — Taft Stettinius & Hollister LLP

(57) ABSTRACT

The present disclosure generally relates to pharmaceutical compositions and/or formulations useful for the treatment of diseases and disorders. More particularly, the disclosure relates to pharmaceutical compositions and/or formulations comprising the cinnamic acid analogue, cinnamein, for the treatment of glycine encephalopathy and urea cycle disorders.

13 Claims, 5 Drawing Sheets

USE OF A CINNAMEIN COMPOSITION FOR THE TREATMENT OF GLYCINE ENCEPHALOPATHY AND UREA CYCLE DISORDERS

CROSS-REFERENCE TO RELATED APPLICATIONS

This application is a Continuation-In-Part of PCT/US21/56799, filed Oct. 27, 2021, which claims the benefit of U.S. Provisional Patent Application No. 63/106,456, filed Oct. 28, 2020, the contents of which are incorporated into the present application in their entirety.

FIELD OF THE INVENTION

The present disclosure generally relates to pharmaceutical compositions and/or formulations useful for the treatment of diseases and disorders. More particularly, the disclosure relates to pharmaceutical compositions and/or formulations comprising the cinnamic acid analogue, cinnamein, for the treatment of glycine encephalopathy and urea cycle disorders.

BACKGROUND

Nonketotic hyperglycinemia (NKH) or glycine encephalopathy is a rare inborn error of metabolism, which is caused by the deficiency of glycine cleavage system. Most of the cases are caused by mutations in the glycine decarboxylase (GLDC) gene. Therefore, biochemically, NKH is characterized by markedly elevated level of glycine in in blood, brain, and cerebrospinal fluid. Due to such increase in glycine, NKH always exhibits complex and diverse phenotypes, such as seizures, hypotonia, cognitive impairment, developmental delays, and myoclonic jerks, ultimately leading to apnea and even death in infancy or early childhood.

Similarly, urea cycle disorders (UCD) are a group of diseases in which affected individuals cannot remove ammonia from their body generated from protein metabolism, ultimately leading to brain damage. Sodium benzoate is the only available drug for glycine encephalopathy. Sodium benzoate is also one of the drugs used for UCD. However, the main problem is that sodium benzoate itself is also quickly excreted out from the body through urine. Therefore, patient is treated with sodium benzoate several times a day at high doses to maintain its effective concentration in the blood. Due to such a high dose sodium benzoate, patients feel drowsy and also suffer from nausea, vomiting and headache.

Cinnamon, the brown bark of cinnamon tree, is a commonly used spice and flavoring material for dessert, candies, chocolate etc. It has a long history of being used as medicine as well. Medieval physicians used cinnamon in medicines to treat a variety of disorders, including arthritis, coughing, hoarseness, sore throats, etc. In addition to containing manganese, dietary fiber, iron, and calcium, cinnamon contains three major compounds-cinnamaldehyde, cinnamyl acetate and cinnamyl alcohol. After intake, these three active compounds are converted into cinnamic acid by oxidation and hydrolysis, respectively. Then, cinnamic acid is β-oxidized to benzoate in the liver. This benzoate exists as sodium salt (sodium benzoate) or benzoyl-CoA.

Sodium benzoate is a widely-used food preservative due to its anti-microbial properties. It also has medical importance as a component of Ucephan™, a Food and Drug Administration (FDA)-approved drug used in the treatment for hepatic metabolic defects associated with hyperammonemia, such as urea cycle disorder. The present inventor explored a novel use of sodium benzoate in treating the disease process of relapsing-remitting EAE in female SJL/J mice (see Brahmachari and Pahan, "Sodium benzoate, a food additive and a metabolite of cinnamon, modifies T cells at multiple steps and inhibits adoptive transfer of experimental allergic encephalomyelitis," J. Immunol., 2007, Jul. 1; 179(1):275-83).

However, sodium benzoate suffers from the problem that it is quickly metabolized and excreted from the body. WO2019070478, also from the current inventor, discloses the unique discovery that glyceryl dibenzoate and glyceryl tribenzoate provide a sustained-release and a slow-release form of sodium benzoate, which allows for a reduced administration regime and improved patient compliance in patients suffering from glycine encephalopathy. Similarly, WO2015109215, also from the current inventor, discloses the unique discovery that glyceryl dibenzoate and glyceryl tribenzoate provide a sustained-release and a slow-release form of sodium benzoate, in patients suffering from urea cycle disorders.

Cinnamein, also known as benzyl cinnamate, 3-phenyl-2-propenoic acid phenylmethyl ester, is the benzyl ester derivative of the reaction of cinnamic acid and benzyl alcohol. Naturally, cinnamein is present in Balsam of Peru and Tolu Balsam. Uses of cinnamein include perfumes and as a flavoring agent. See Fahlbusch et al., (2007), "Flavors and Fragrances,' in Ullmann's Encyclopedia of Industrial Chemistry (7th ed.), Wiley, p. 59. Pharmacologically, cinnamein has antibacterial and antifungal properties and is the key ingredient in the over-the-counter anti-rash cream, SUDOCREM® (sudocrem.com; see also, Korošec et al., (2014), "Antifungal activity of cinnamic acid derivatives involves inhibition of benzoate 4-hydroxylase (CYP53), J Applied Microbio. 116 (4): 955-966).

However, there are no other studies describing other pharmaceutical uses. The present disclosure addresses this lack of information.

SUMMARY OF THE DISCLOSURE

The inventors have discovered methods and pharmaceutical compositions and/or formulations useful for the treatment of diseases and disorders, in particular, treatment of glycine encephalopathy (or NKH, used interchangeably herein) and urea cycle disorders. More particularly, the present disclosure relates to methods and pharmaceutical compositions and/or formulations comprising the cinnamic acid analogue, cinnamein and or cinnamic acid, for the treatment of glycine encephalopathy and urea cycle disorders.

Since cinnamein is the benzyl derivative of cinnamate, in the body, this compound is metabolized such that the ester bond is hydrolyzed to produce cinnamic acid and benzyl alcohol. Furthermore, while benzyl alcohol is transformed into benzoic acid by direct oxidation, cinnamic acid undergoes β-oxidation to be converted into benzoic acid. Benzoic acid will remain as sodium benzoate that will scavenge glycine in conditions such as glycine encephalopathy and urea cycle disorders to remove it as hippuric acid through the urine. Thus, one molecule of cinnamein produces one molecule of cinnamic acid and one molecule of sodium benzoate. The inventors have taken advantage of this metabolic pathway for cinnamein in order to utilize is a prodrug of both cinnamic acid and sodium benzoate and this useful for the treatment of glycine encephalopathy and urea cycle disorders.

In one embodiment, a method for treating glycine encephalopathy is provided. The method comprises administering to a patient in need thereof an effective amount of a pharmaceutical composition comprising cinnamein and/or cinnamic acid.

In another embodiment, a method for treating or inhibiting the progression of a urea cycle disorder is disclosed. The method comprises administering to a patient in need thereof an effective amount of a pharmaceutical composition comprising cinnamein and/or cinnamic acid.

In still another embodiment of the invention, pharmaceutical compositions are provided where the compositions comprise an effective amount of cinnamein and/or cinnamic acid.

In still yet another embodiment of the invention are provided methods for the manufacture of medicaments useful for the treatment of glycine encephalopathy and urea cycle disorders.

These and other embodiments and features of the disclosure will become more apparent through reference to the following description, the accompanying figures, and the claims. Furthermore, it is to be understood that the features of the various embodiments described herein are not mutually exclusive and can exist in various combinations and permutations.

BRIEF DESCRIPTION OF THE DRAWINGS

FIG. 1B, distance traveled; FIG. 1C, velocity; FIG. 1D, center zone frequency). Results are mean+SEM of five mice per group. *p<0.05; p<0.01; *p<0.001.

FIG. 4B, errors; FIG. 4C, latency). Results are mean+SEM of three mice per group. ***p<0.001.

DETAILED DESCRIPTION

Figures 1A, 1B, 1C, 1D:
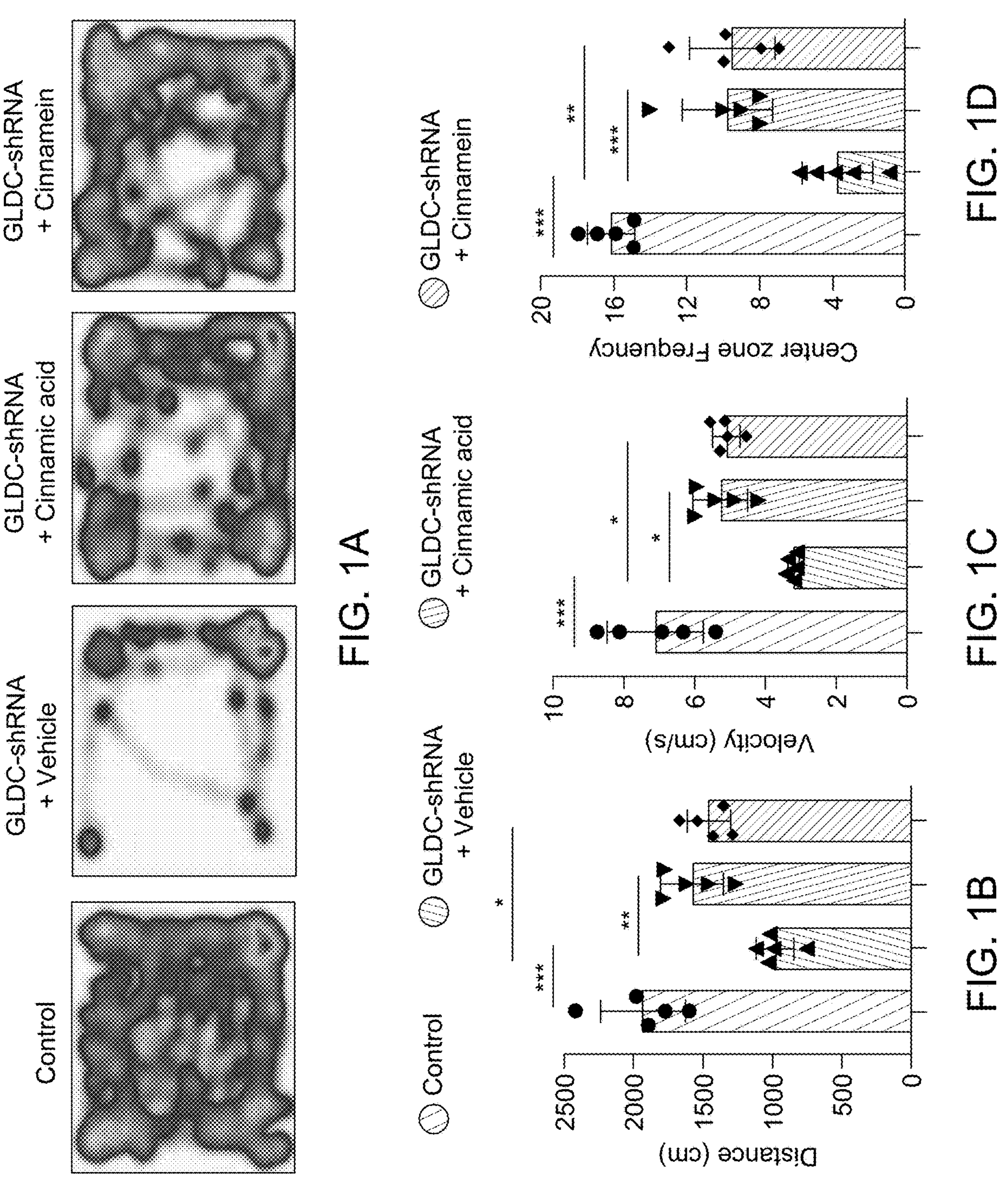
FIG. 1A-D shows that oral administration of cinnamein and cinnamic acid improves locomotor activities in Lenti-GLDC-shRNA-insulted mice. C57/BL6 mice (8-10 week old) received lentiviral GLDC shRNA (1×107 IFU/mouse in 100 μl HBSS) once via tail-vein injection. Therefore, control mice also received 100 μl HBSS via tail-vein. From 7 d after lenti-GLDC shRNA injection, mice were treated with cinnamein (50 mg/kg body wt/d) and cinnamic acid (50 mg/kg body wt/d) daily via gavage. After 10 d of treatment, locomotor activities were monitored by open field (FIG. 1A, heat map.

Throughout this disclosure, various quantities, such as amounts, sizes, dimensions, proportions, and the like, are presented in a range format. It should be understood that the description of a quantity in range format is merely for convenience and brevity and should not be construed as an inflexible limitation on the scope of any embodiment. Accordingly, the description of a range should be considered to have specifically disclosed all the possible subranges as well as all individual numerical values within that range unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 4.62, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "includes", "comprises", "including" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C).

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The present disclosure is based on the discovery that methods and pharmaceutical compositions and/or formulations comprising the cinnamic acid analogue, cinnamein and or cinnamic acid, are useful for the treatment of glycine encephalopathy and urea cycle disorders. Specifically, the inventor discovered that using a mouse model simulating glycine encephalopathy (i.e. NKH-like) and urea acid disorders, namely elevated blood glycine levels, conditions in created by tail-vein injection of lentiviral glycine decarboxylase shRNA, cinnamein as well as cinnamic acid can reduce the level of glycine from blood and brain and thus protect mice from NKH (glycine encephalopathy) and urea acid disorders.

The methods and treatments disclosed herein comprise administering an effective amount of a pharmaceutical composition comprising cinnamein and/or cinnamic acid to a patient in need thereof. In accordance with the present disclosure, the treatment may be administered one time per day. In some aspects, the treatment may include a twice daily administration. In other aspects, treatment may include three or more times daily administration.

In the treatment methods contemplated by the present disclosure, cinnamein and/or cinnamic acid may be used alone or in compositions together with a pharmaceutically acceptable carrier or excipient. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Other suitable pharmaceutically acceptable excipients are described in "Remington's Pharmaceutical Sciences," Mack Pub. Co., New Jersey, 1991, the contents of which are expressly incorporated herein by reference.

In certain embodiments, the cinnamein and/or cinnamic acid may be orally administered to humans and other animals. The cinnamein and/or cinnamic acid may be formulated for administration and methods of formulation are well known in the art (see, for example, *Remington: The Science and Practice of Pharmacy*, Mack Publishing Company, Easton, Pa., 19th Edition (1995)).

Any of the formulations disclosed herein can be used for treating/inhibiting the progression of glycine encephalopathy and urea cycle disorders.

In some embodiments, the present disclosure relates to a method of using a formulation for inhibiting the progression of glycine encephalopathy and urea cycle disorders. The methods comprise administering to a patient in need thereof an effective amount of the formulation. In some embodiments, the formulation comprises 0.0001 to 100 g of cinnamein and/or cinnamic acid. In some embodiments, the formulation may comprise only cinnamein as an active ingredient, in others the formulation may comprise both cinnamein and cinnamic acid.

In some embodiments, the formulations may be sustained-release formulations, meaning that they release cinnamein and/or cinnamic acid steadily over an extended period of time. In other embodiments, the formulations may be delayed-release formulations, meaning that they release cinnamein and/or cinnamic acid at a time later than that immediately following its administration.

In some embodiments, the formulations are administered orally to the patient. In some embodiments, the total daily dose could be divided into multiple doses, such as two or three substantially equal doses, and administered at different times throughout a day.

Pharmaceutical compositions for use in accordance with the present disclosure can be in the form of sterile, non-pyrogenic liquid solutions or suspensions, coated capsules, lyophilized powders, or other forms known in the art.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinyl-pyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art.

In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Effective amounts of the compositions of this disclosure generally include any amount sufficient to inhibit (e.g. slow or stop) the progression of glycine encephalopathy and urea cycle disorders. The amount of active ingredient (cinnamein and/or cinnamic acid) that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disorder or disease undergoing therapy. The therapeutically effective amount for a given situation can be readily determined by routine experimentation and is within the skill and judgment of the ordinary clinician.

According to the methods of treatment of the present disclosure, progression of the disorder is slowed or stopped in a patient, such as a human or lower mammal, by administering to the patient an effective amount of the cinnamein and/or cinnamic acid in such amounts, and for such time as is necessary, to achieve the desired result. An amount of a compound that is effective to slow or stop the progression of a disease or disorder may refer to a sufficient amount of the compound to treat the disease or disorder at a reasonable benefit/risk ratio applicable to any medical treatment.

It will be understood, however, that the total daily dosage of the compounds and compositions of the present disclosure will be decided by the attending physician within the scope of sound medical judgment. The specific therapeutically effective dose level for any particular patient will depend upon a variety of factors including the disease or disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The "effective amount" or dose of a compound of the present disclosure, such as cinnamein and/or cinnamic acid, to be administered to warm-blooded animals, such as humans, may vary depending upon the disorder to be treated. In connection with glycine encephalopathy and urea cycle disorders, the effective amount of the cinnamein and/or cinnamic acid may be from approximately 0.001 g to approximately 100 g per day.

In one aspect of the present disclosure, a treatment is disclosed for inhibiting the progression of urea cycle disorders. A urea cycle disorder is a genetic disorder caused by a deficiency of one of the enzymes in the urea cycle that is responsible for removing ammonia from the blood stream. There are six know disorders of the urea cycle. Each can be classified by the initials of the missing enzyme. Thus, the six known urea disorders may be referred to as N-acetylglutamate synthase (NAGS), Carbamoyl Phosphate Synthetase 1 (CPS1), Ornithine transcarbamoylase (OTC), Argininosuccinate synthase (ASS), argininosuccinate lyase (ASL), and Arginase 1 (ARG1). The treatment comprises administering an effective amount of a pharmaceutical composition comprising cinnamein and/or cinnamic acid to a patient in need thereof.

Further reference is made to the following experimental examples.

EXAMPLES

The following examples are given for the purpose of illustrating various embodiments of the invention and are not meant to limit the present disclosure in any fashion. The present examples, along with the methods described herein are presently representative of preferred embodiments, are provided only as examples, and are not intended as limitations on the scope of the invention. Changes therein and other uses which are encompassed within the spirit of the disclosure as defined by the scope of the claims will occur to those skilled in the art.

Example 1

Treatment of C57/BL6 Mice with Lentiviral Glycine Decarboxylase (GLDC) shRNA

C57/BL6 mice (8-10 week-old) received lentiviral GLDC shRNA (1×107 IFU/mouse in 100 μl Hank's Balanced Salt Solution or HBSS) once via tail-vein injection. The group of control mice received only 100 μl HBSS via tail-vein injection. Oral administration of cinnamein occurred from 7 d after lenti-GLDC shRNA injection. Mice were treated with 50 mg/kg body wt/d of cinnamein daily via gavage. Cinnamein (Sigma) was solubilized in 100 μl 0.5% methyl cellulose before gavage. Therefore, one group of lenti-GLDC shRNA-insulted mice were also treated with 100 μl 0.5% methyl cellulose as vehicle control. For comparison, one group of lenti-GLDC shRNA-insulted mice were also treated with 50 mg/kg body wt/d of cinnamic acid daily via gavage.

After 10 d of treatment with cinnamein and cinnamic acid, mice were monitored for locomotor activities by open field test. Briefly, each mouse was allowed to freely explore an open field arena for 5 min. The testing apparatus was a classic open field (i.e., a wooden floor square arena, 40×40 cm, with walls 30 cm high). A video camera connected to a computer system was placed above the box. Each mouse was placed individually on the center of the arena and the performance was monitored by the live video tracking system. The results are shown in FIG. 1A-D.

FIG. 1A-D shows that oral administration of cinnamein and cinnamic acid improves locomotor activities in Lenti-GLDC-shRNA-insulted mice: FIG. 1A, heat map; FIG. 1B, distance traveled; FIG. 1C, velocity; FIG. 1D, center zone frequency. As evident from heat map (FIG. 1A), total distance travelled (FIG. 1B), velocity (FIG. 1C), and center zone frequency (FIG. 1D), significant locomotor impairment was seen in lenti-GLDC shRNA-insulted mice in comparison to HBSS-treated control mice (FIG. 1A). However, oral administration of both cinnamein and cinnamic acid improved locomotor activities in lenti-GLDC shRNA-insulted mice.

Next, mice were monitored for spatial learning and memory by Barnes maze. Here, mice were trained for two consecutive days followed by examination on day three. During training, the overnight food-deprived mouse was placed in the middle of the maze in a 10 cm high cylindrical start chamber. After 10 s, the start chamber was removed to allow the mouse to move around the maze to find out the color food chips in the baited tunnel.

Figures 2A, 2B, 2C:
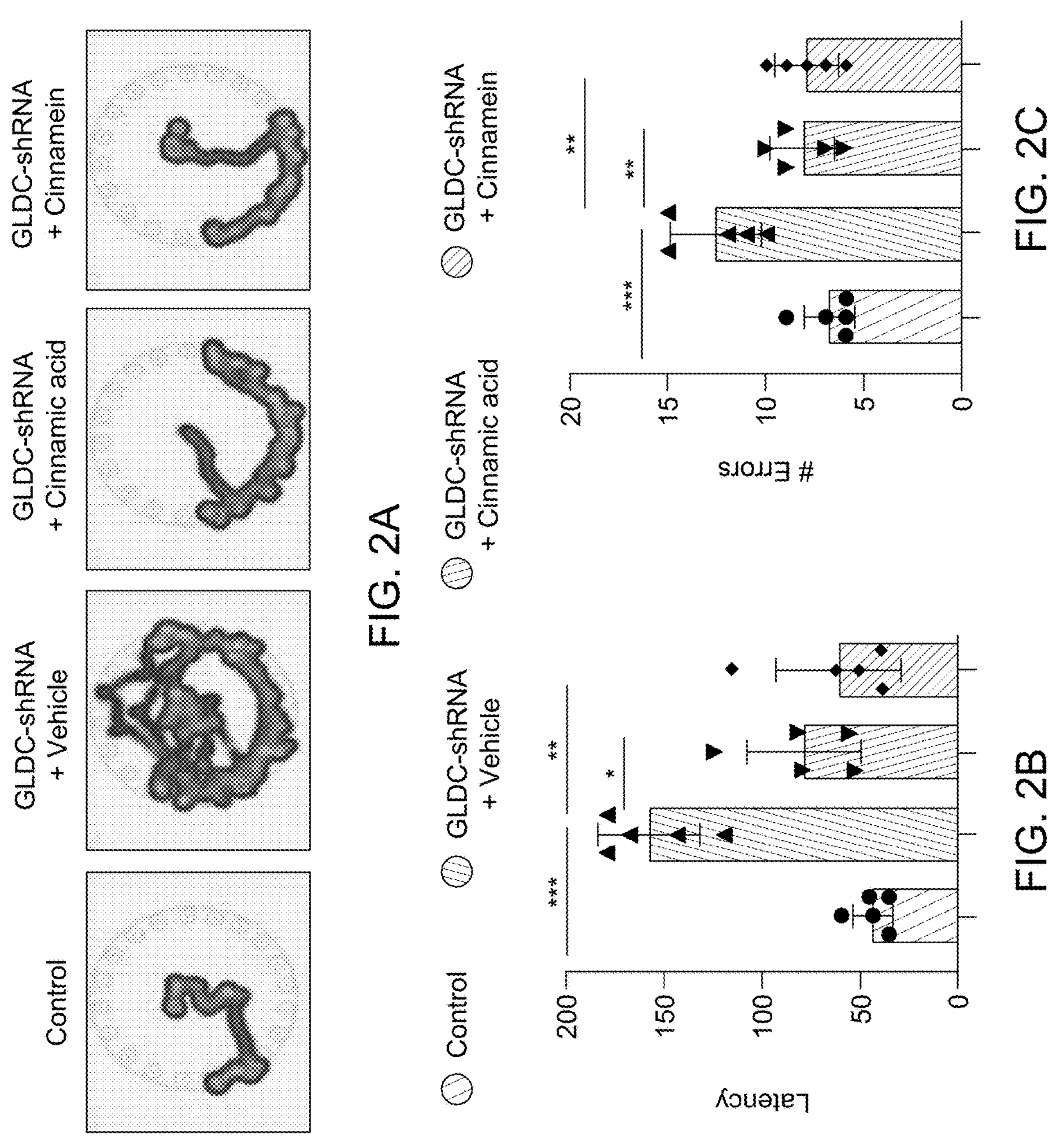
FIG. 2A-C shows that oral administration of cinnamein and cinnamic acid recovers cognitive functions in Lenti-GLDC-shRNA-insulted mice. C57/BL6 mice (8-10 week old) received lentiviral GLDC shRNA (1×107 IFU/mouse in 100 μl HBSS) once via tail-vein injection. Therefore, control mice also received 100 μl HBSS via tail-vein. From 7 d after lenti-GLDC shRNA injection, mice were treated with cinnamein (50 mg/kg body wt/d) and cinnamic acid (50 mg/kg body wt/d) daily via gavage. After 10 d of treatment, spatial learning and memory was monitored by Barnes maze (A, heat map; B, latency; C, errors). Results are mean+SEM of five mice per group. *p<0.05; p<0.01; *p<0.001.

The results are shown in FIG. 2A-C. Significant cognitive impairment was seen in lenti-GLDC shRNA-insulted mice as compared to HBSS-treated control mice. Lenti-GLDC shRNA-insulted mice took longer time to find the correct hole (FIG. 2A, FIG. 2B) and made more errors (FIG. 2C) as compared to HBSS-treated control mice. However, oral cinnamein and cinnamic acid significantly reduced latency and errors of lenti-GLDC shRNA-insulted mice in reaching the target hole, suggesting that oral cinnamic acid also increased cognitive functions of lenti-GLDC shRNA-insulted mice.

Figures 3A, 3B:
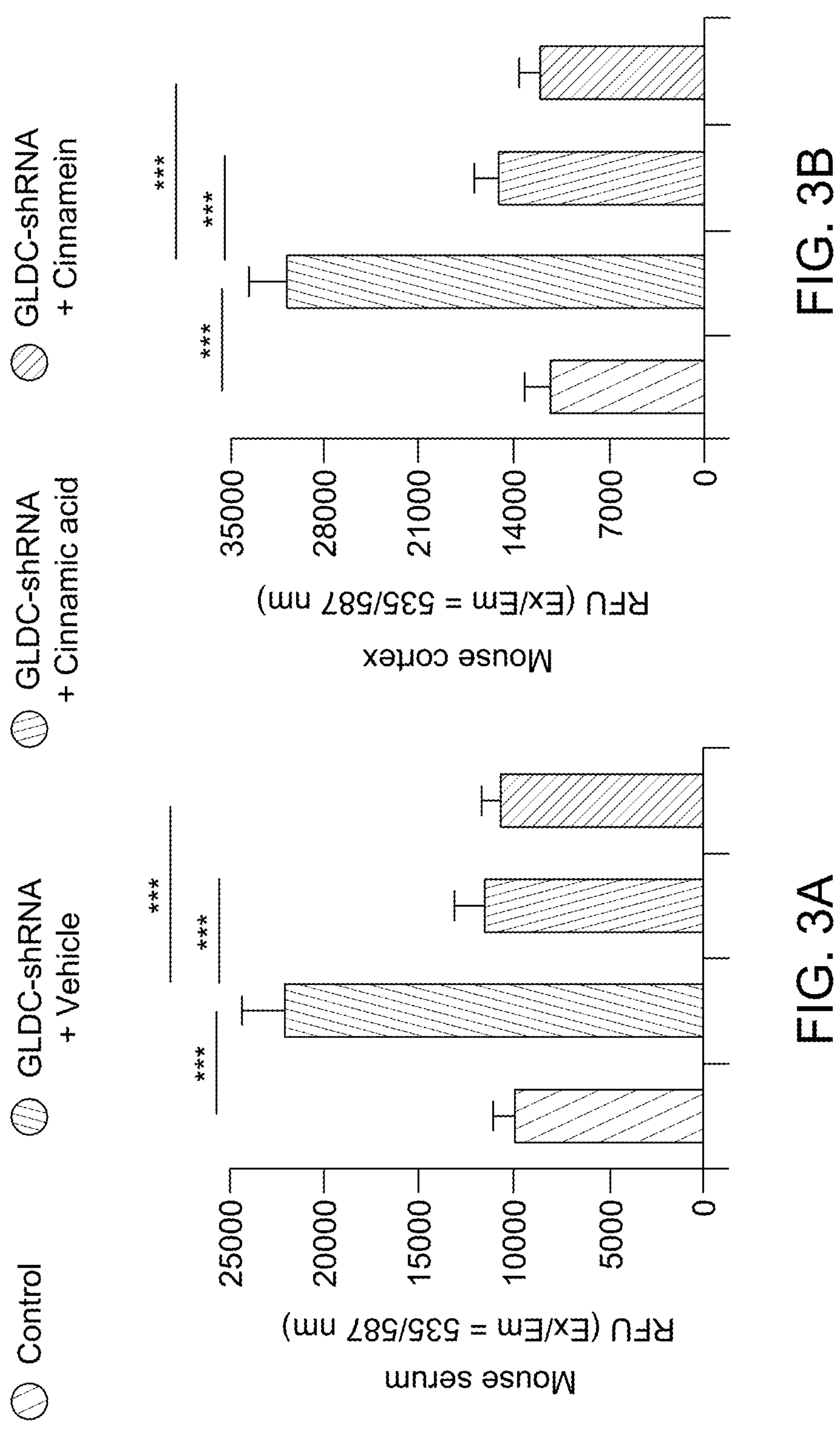
FIGS. 3A and B show that oral administration of cinnamein and cinnamic acid reduces the level of glycine in serum and cortex of lenti-GLDC-shRNA-insulted mice. C57/BL6 mice (8-10 week old) received lentiviral GLDC shRNA (1×107 IFU/mouse in 100 μl Hank's Balanced Salt Solution or HBSS) once via tail-vein injection. Therefore, control mice also received 100 μl HBSS via tail-vein. From 7 d after lenti-GLDC shRNA injection, mice were treated with cinnamein (50 mg/kg body wt/d) and cinnamic acid (50 mg/kg body wt/d) daily via gavage. After 14 d of treatment, the level of glycine was measured in serum (A) and cortex (B) by using a fluorometric assay kit (Biovision). Each mouse sample was run in triplicate. Results are mean+SEM of five mice per group. ***p<0.001.

On 14 d of treatment, mice were sacrificed, and level of glycine was measured in serum and brain. As expected, markedly increased levels of glycine were observed in serum (FIG. 3A) and cortex (FIG. 3B) of lenti-GLDC shRNA-insulted mice as compared to control mice receiving only HBSS. However, treatment with cinnamein and cinnamic acid significantly inhibited the level of glycine in both serum (FIG. 3A) and cortex (FIG. 3B) of lenti-GLDC shRNA-insulted mice. No other side effects were observed in any of the mice during drug treatment including hair loss, weight loss, diarrhea, or untoward infection.

Example 2

Treatment of Ornithine Transcarbamylase (OTC) Knockout Mice with Cinnamein or and Cinnamic Acid Cognitive deficit is common in individuals with inherited urea cycle disorders (UCDs). The inventors demonstrate that oral administration of cinnamein or benzyl cinnamate and cinnamic acid improves memory and learning in ornithine transcarbamylase (OTC) knockout mice, an animal model of UCD. See for example Qureshi et al., "Ornithine Transcarbamylase Deficiency in Mutant Mice I. Studies on the Characterization of Enzyme Defect and Suitability as Animal Model of Human Disease," (1979) Pediat. Res. 13: pp 807-811; Hodges et al., "The spfash mouse: A missense mutation in the ornithine transcarbamylase gene also causes aberrant mRNA splicing." (1989) Proc. Natl. Acad. Sci. USA 86: pp. 4142-4146. OTC knockout B6EiC3Sn a/A-Otcspf-ash/J (Otcspf-ash) mice were obtained from the Jackson Lab. Cinnamein was purchased from Sigma. Cinnamic acid was bought from Spectrum Chemicals.

Figure 4A:
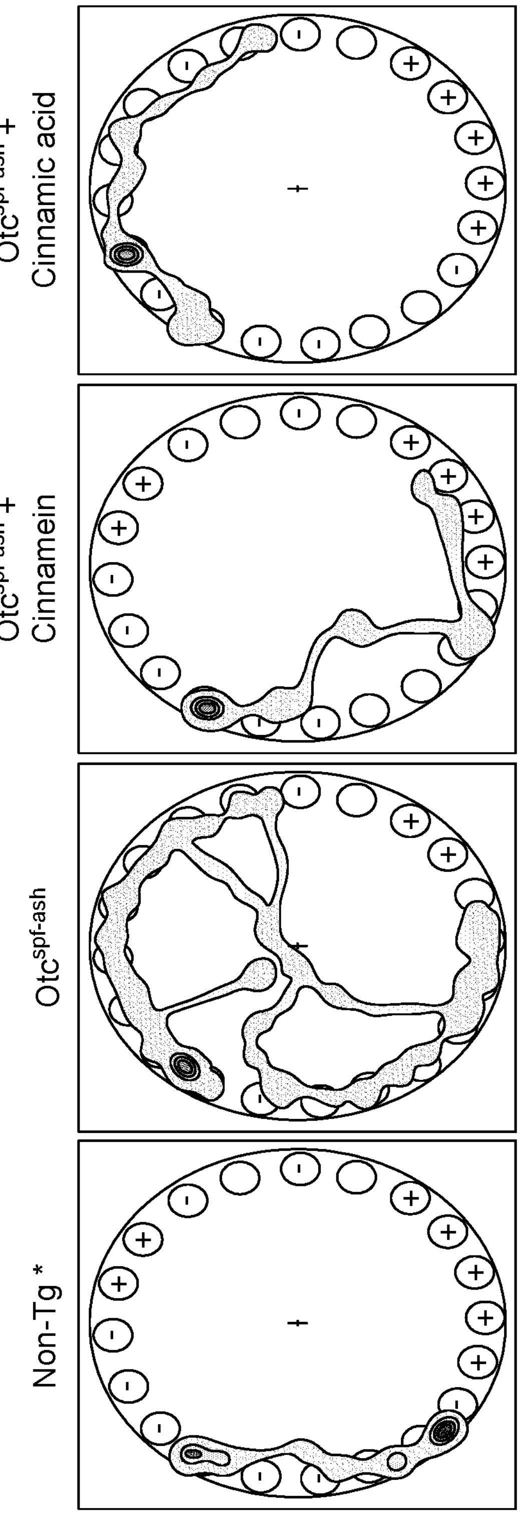
FIG. 4A-C demonstrate that oral administration of cinnamein and cinnamic acid recovers cognitive functions in an animal model of urea cycle disorders. Eight-week old B6EiC3Sn a/A-Otc$^{spf-ash}$/J (Otc$^{spf-ash}$) mice were treated with cinnamein (50 mg/kg body weight/d) and cinnamic acid (50 mg/kg body weight/d) orally via gavage for 15 days followed by monitoring cognitive functions by Barnes maze (FIG. 4A, representative track plots summarizing the overall activity of mice on the apparatus recorded with a Noldus camera and visualized by Ethovision XT software.
Figures 4B, 4C:
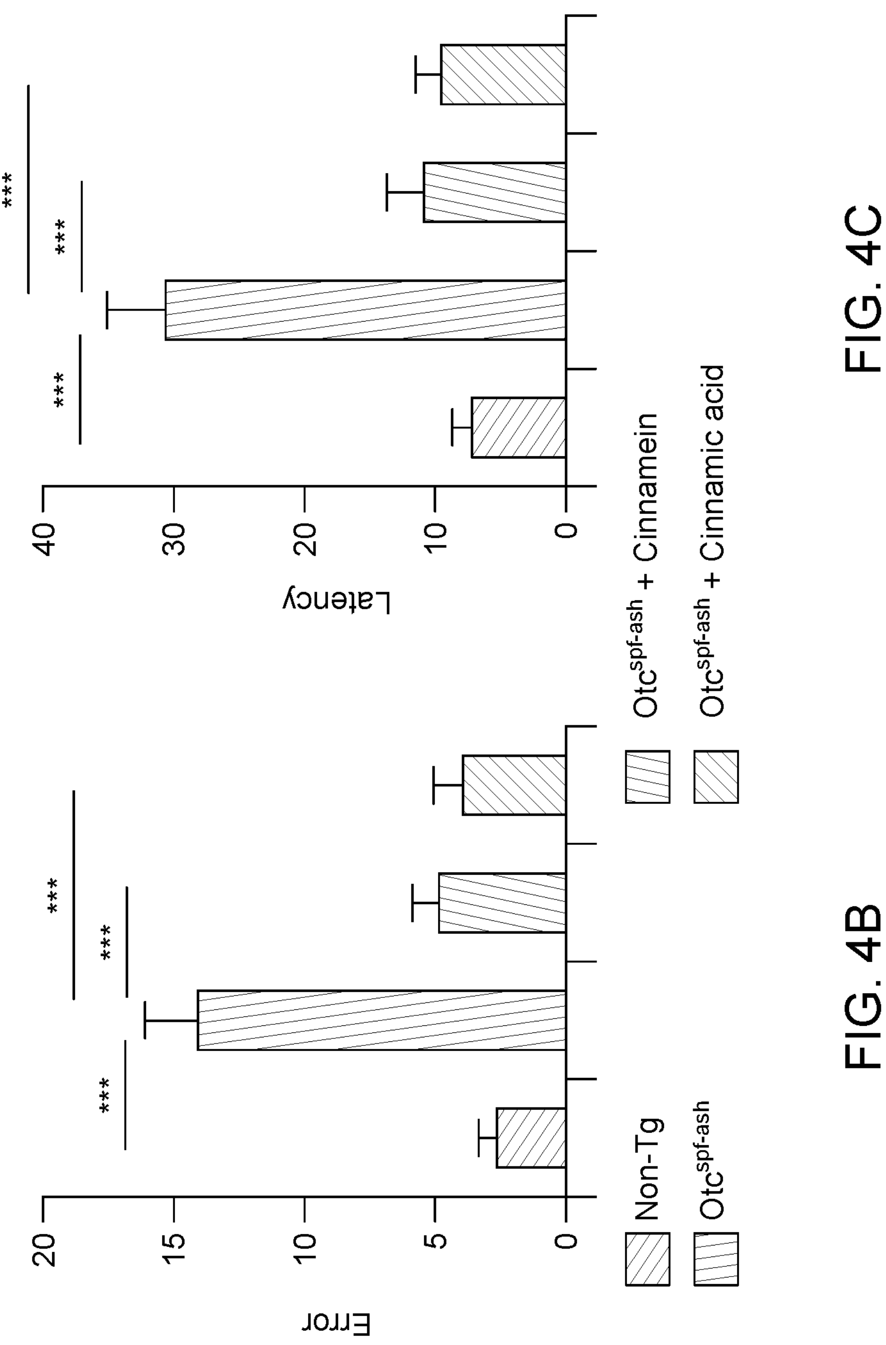

FIG. 4A-C demonstrate that oral administration of cinnamein and cinnamic acid recovers cognitive functions in an animal model of urea cycle disorders. Eight-week old B6EiC3Sn a/A-Otcspf-ash/J (Otcspf-ash) mice were treated with cinnamein (50 mg/kg body weight/d) and cinnamic acid (50 mg/kg body weight/d) orally via gavage for 15 days followed by monitoring cognitive functions by Barnes maze (FIG. 4A, representative track plots summarizing the overall activity of mice on the apparatus recorded with a Noldus camera and visualized by Ethovision XT software; FIG. 4B, errors; FIG. 4C, latency). Results are mean+SEM of three mice per group. ***$p<0.001$.

Together, these data indicate therapeutic potential of the use of cinnamein in glycine encephalopathy and urea cycle disorders.

As will be appreciated from the descriptions herein, a wide variety of aspects and embodiments are contemplated by the present disclosure, examples of which include, without limitation, the aspects and embodiments listed below:

A method for treating glycine encephalopathy is provided. The method comprises administering to a patient in need thereof an effective amount of a pharmaceutical composition comprising cinnamein and/or cinnamic acid.

A method for treating or inhibiting the progression of a urea cycle disorder is provided. The method comprises administering to a patient in need thereof an effective amount of a pharmaceutical composition comprising cinnamein and or cinnamic acid.

Pharmaceutical compositions are provided where the compositions comprise an effective amount of cinnamein and/or cinnamic acid.

Methods for the manufacture of medicaments useful for the treatment of glycine encephalopathy and urea cycle disorders are provided.

While embodiments of the present disclosure have been described herein, it is to be understood by those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for inhibiting the progression of a urea cycle disorder comprising administering to a patient in need thereof an effective amount of a pharmaceutical composition comprising cinnamein and/or cinnamic acid.

2. The method of claim 1, wherein the pharmaceutical composition is administered to the patient at least one time per day.

3. The method of claim 1, wherein the effective amount is from about 0.001 grams to about 100 grams per day.

4. The method of claim 1, wherein the pharmaceutical composition is formulated together with a pharmaceutically acceptable carrier or excipient.

5. The method of claim 1, wherein the pharmaceutical composition is administered orally.

6. The method of claim 1, wherein the urea cycle disorder is selected from the group consisting of N-acetylglutamate synthase deficiency, Carbamoyl Phosphate Synthetase 1 deficiency, Ornithine transcarbamoylase deficiency, Argininosuccinate synthase deficiency, argininosuccinate lyase deficiency, Arginase 1 deficiency, and any combination thereof.

7. A method for inhibiting the progression of a urea cycle disorder comprising administering to a patient in need thereof an effective amount of a pharmaceutical composition comprising cinnamein.

8. The method of claim 7, wherein the composition further comprises cinnamic acid.

9. The method of claim 7, wherein the pharmaceutical composition is administered to the patient at least one time per day.

10. The method of claim 7, wherein the effective amount is from about 0.001 grams to about 100 grams per day.

11. The method of claim 7, wherein the pharmaceutical composition is formulated together with a pharmaceutically acceptable carrier or excipient.

12. The method of claim 7, wherein the pharmaceutical composition is administered orally.

13. The method of claim 7, wherein the urea cycle disorder is selected from the group consisting of N-acetylglutamate synthase deficiency, Carbamoyl Phosphate Synthetase 1 deficiency, Ornithine transcarbamoylase deficiency, Argininosuccinate synthase deficiency, argininosuccinate lyase deficiency, Arginase 1 deficiency, and any combination thereof.

* * * * *